United States Patent [19]

Vanderhoof

[11] Patent Number: 4,846,811
[45] Date of Patent: Jul. 11, 1989

[54] SLIDING SHEATH FOR MEDICAL NEEDLES

[75] Inventor: Merton J. Vanderhoof, Balboa Island, Calif.

[73] Assignee: International Medical Innovators, Inc., San Clemente, Calif.

[21] Appl. No.: 8,308

[22] Filed: Jan. 29, 1987

[51] Int. Cl.[4] .............................................. A61M 5/00
[52] U.S. Cl. ...................................... 604/263; 604/198
[58] Field of Search .............. 604/110, 162, 192, 198, 604/263

[56] References Cited

U.S. PATENT DOCUMENTS

| | | | |
|---|---|---|---|
| 2,571,653 | 10/1951 | Bastien | 128/218 |
| 2,592,744 | 6/1986 | Jagger et al. | 604/192 |
| 2,847,995 | 8/1958 | Adams | 128/214 |
| 2,847,996 | 8/1958 | Cohen | 128/218 |
| 2,888,923 | 6/1959 | Da Cunha Reis | 128/218 |
| 3,306,290 | 2/1967 | Weltman | 128/218 |
| 3,306,291 | 2/1967 | Burke | 128/218 |
| 3,356,089 | 12/1967 | Francis | 128/221 |
| 3,485,239 | 12/1969 | Vanderbeck | 128/218 |
| 3,536,073 | 10/1970 | Farb | 604/162 |
| 3,780,734 | 12/1973 | Wulff | 128/218 |
| 3,884,230 | 5/1920 | Wulff | 128/221 |
| 3,890,971 | 6/1975 | Leeson | 128/218 |
| 4,139,009 | 2/1979 | Alvarez | 128/218 |
| 4,170,993 | 10/1979 | Alvarez | 604/263 X |
| 4,266,543 | 5/1981 | Blum | 128/218 |
| 4,266,544 | 5/1981 | Wardlaw | 128/218 |
| 4,273,123 | 6/1981 | Lemelson | 128/218 |
| 4,356,822 | 12/1982 | Winstead-Hall | 128/218 |
| 4,373,526 | 2/1983 | Kling | 128/215 |
| 4,392,859 | 7/1983 | Dent | 604/198 |
| 4,425,120 | 1/1984 | Sampson et al. | 604/263 X |
| 4,425,120 | 1/1984 | Sampson et al. | 604/198 |
| 4,430,080 | 2/1984 | Pasquini et al. | 604/263 X |
| 4,507,117 | 3/1985 | Vining et al. | 604/196 |
| 4,573,976 | 3/1986 | Sampson et al. | 604/198 |
| 4,631,057 | 12/1986 | Mitchell | 604/198 |
| 4,643,199 | 2/1987 | Jennings, Jr. | 128/763 |
| 4,659,330 | 4/1987 | Nelson et al. | 604/192 |
| 4,664,259 | 5/1987 | Landis | 206/365 |
| 4,675,005 | 6/1987 | Deluccia | 604/110 |
| 4,676,783 | 6/1987 | Jagger et al. | 604/162 X |
| 4,676,783 | 6/1987 | Jagger et al. | 604/171 |
| 4,681,567 | 7/1987 | Masters et al. | 604/198 |

Primary Examiner—Dalton L. Truluck
Attorney, Agent, or Firm—Stetina and Brunda

[57] ABSTRACT

Apparatus and methods of utilizing the same to prevent accidental medical needle sticks are disclosed, characterized by use of a raised locking member coaxially mounted upon the needle approximately midway between a body member mounting the needle and the needle tip which presents an exterior contour to engage complementary features within the interior channel of a tubular sleeve which slides coaxially along the needle. The slidable sleeve is held at a first position proximate the body member and exposing the needle tip by a mechanical detent formed from frictional engagement of complementary surfaces upon the sleeve and the locking member and/or the body member. After medical use, the spent and contaminated needle is sheathed by sliding the tubular sleeve to a second position wherein it is securely held by a detent resultant from engagement with the locking member. The sheathing guards against accidental needle sticks transmitting disease. An optional end cap may be affixed including frangible affixation by engagement with the locking member, slidable sleeve, or body member. All components may be readily retrofitted upon preexisting needles.

30 Claims, 2 Drawing Sheets

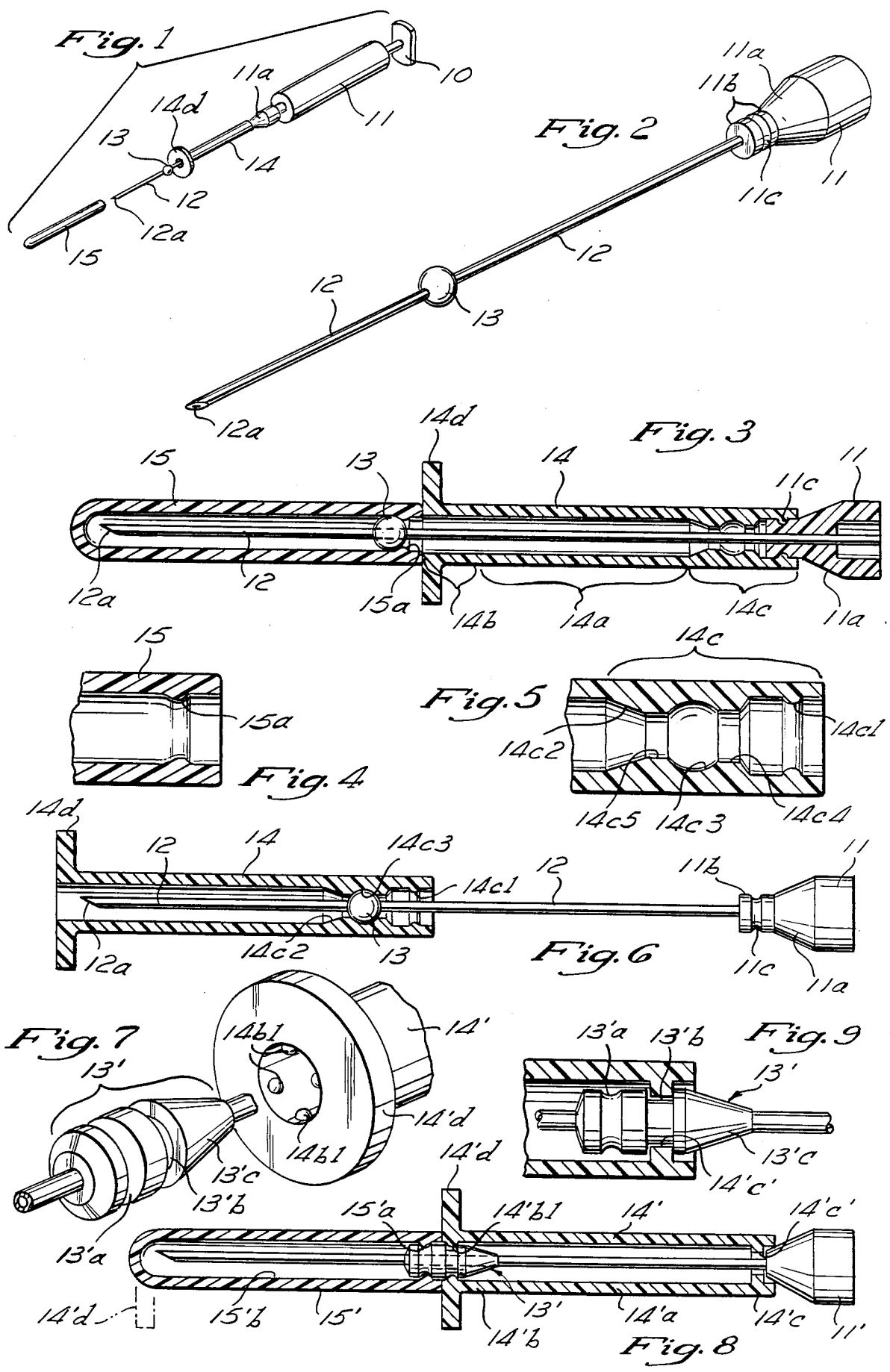

SLIDING SHEATH FOR MEDICAL NEEDLES

BACKGROUND OF THE INVENTION

1. Field of the Invention

The present invention concerns the prevention of disease transmission occurring from accidental sharp, or needle sticks with spent or contaminated medical needles.

2. Description of Relevant Art

Accidental needle stick injuries are common amongst health care workers such as doctors, nurses, laboratory personnel, and housekeeping personnel. Accidental needle sticks with contaminated needles can result in the transmission of diseases including Acquired Immune Deficiency Syndrome (AIDS), Hepatitis B, Non-A-Non-B Hepatitis, and other diseases transmissable through the blood. The severe health hazards and consequences associated with these diseases have resulted in well-thought-out protocols for handling medical needles and a near universal use of needle and syringe disposal containers.

Notwithstanding the care taken with contaminated medical needles, it is estimated in the publication *Bio-Medical International*, Vol. IX. 23-24 for December, 1986 that "an estimated 800,000 sharp or needle sticks occur each year in the U.S.". It is further estimated that "primary treatment (glamma globulin, hepatitis B immune globulin, tetanus) and subsequent blood analysis and care costs ... $600–$1,000 per incident". This figure may be compared with a similar report that "each needle stick injury costs a hospital more than $200.00" in U.S. Pat. No. 4,592,744 filed Aug. 14, 1985. Whatsoever the actual prevalence and actual cost of an accidental needle stick injury, it is indisputable that each such injury is psychologically disconcerting to the health care worker receiving the injury.

Accidental needle sticks may often occur when a drawer of blood, or any administrator injecting a patient, attempts to recap or dispose of a needle, syringe, or vacuum tube phlebotomy system after use. Although modern health care protocols seldon allow for any prolonged exposure of a contaminated needle upon a work surface, in some instances a contaminated needle is set upon a work surface by one person, normally the administrator, and subsequently removed for disposal by another person, normally an assistant or nurse. During the course of this handling and interchange accidental self-sticks and sticks of other persons occasionally occur.

In order to reduce the numbers of accidental needle sticks during necessary handling, a number of needle sheathing systems have been developed within the prior art. These systems generally show a sheathing or a resheathing of a needle by dealing with the entire injection apparatus, or syringe, to which the needle is connected. In many instances the needle will be withdrawn within a syringe, or the entire syringe will be covered by sliding covers.

The present invention will be seen to be distinguished from such prior art in one aspect by dealing with the sheathing of a needle directly at and along the length of the needle itself, as opposed to sheathing any syringe or ampoule to which the needle is connected. Particularly, the needle sheating scheme in accordance with the present invention exhibits in a first general embodiment a localized locking member, i.e. a bead or protuberance, rigidly positioned along the length of the needle. The locking member is cooperatively interactive with a sliding tubular sleeve coaxially positioned along the length of the needle in order to selectively retain this sleeve in a position sheathing the end of the needle. Although such a sheathing scheme needs to be given a broad interpretation, and although the means of engaging and retaining a sliding tubular sleeve need not appear exactly as a locking bead or protuberance which is positioned directly upon the needle, the present invention does involve a sleeve which slides along the needle in order to sheath the needle, and a retaining or locking mechanism for such slidable sleeve which retaining mechanism is in a fixed relationship to the needle. This should be contrasted to a prior art sheathing devices which either (i) slide along a syringe, or are (ii) replaceably removable from the needle. By such differences and other differences, the present invention may be observed to comprise a significant unobvious departure from the prior art.

In particular, the following is a list of U.S. Patents which exemplify the current state of art: U.S. Pat. Nos. 4,592,744; 4,507,117; 4,392,859; 4,373,526; 4,273,123; 4,266,544; 4,139,009; 3,890,971; 3,485,239; 3,356,089; 3,306,291; 3,306,290; 2,925,083; 2,888,923; 2,847,966; 2,847,995.

U.S. Pat. No. 4,592,744 shows a syringe which is self-resheathing within a case when the needle is withdrawn.

U.S. Pat. No. 4,507,117 shows a syringe with a needle retractable into the barrel of the syringe.

U.S. Pat. No. 4,392,859 shows an automatic injecting device having a spring-biased retracting needle.

U.S. Pat. No. 4,373,526 shows a protective closure for a hypodermic needle which may receive and retain the needle after it is removed from, or broken off, the end of the syringe.

U.S. Pat. No. 4,266,544 shows a device on the end of a syringe apparatus which renders a needle inoperable subsequent to being used.

U.S. Pat. No. 4,139,009 shows a retractable cover means for a hypodermic.

U.S. Pat. No. 3,890,971 shows a safety feature for syringes which, subsequent to being used, locks the plunger and needle such that it is incapable of being reused.

U.S. Pat. No. 3,485,239 shows a self-contained syringe wherein the hypodermic needle is initially situated within a barrel.

U.S. Pat. No. 3,356,089 shows a needle sheath and guide, particularly for selectable penetration control.

U.S. Pat. No. 3,306,291 shows the use of frangible connections in combination with syringes and the like.

U.S. Pat. No. 3,306,290 shows the use of a spring-biased retractable syringe.

U.S. Pat. No. 2,925,083 shows a hypodermic syringe with a hood for guarding the needle.

U.S. Pat. No. 2,888,293 shows a syringe within a coaxial protective tube.

U.S. Pat. No. 2,847,996 shows the use of a hypodermic having two barrel-like compartments.

U.S. Pat. No. 2,847,995 shows the use of retractable needle within a rubber sheath.

As a further point of comparison of the prior art to the present invention, it should be additionally observed that the referenced patents show unique apparatus constructions which are generally incompatible to be assimilated with or retrofitted upon any pre-existing standard disposable syringe or needle (such as those commonly manufactured by market leaders Becton Dickinson or Sherwood). The present invention is, to the contrary, readily adaptable to pre-existing disposable needles and syringes that are made by major manufacturers. The apparatus of the present invention, in certain variants, is adaptable to such pre-existing needles and syringes by retrofit. Alternatively, the apparatus of the present invention may, in other variants, be directly incorporated in medical needles and syringes upon initial manufacture.

SUMMARY OF THE INVENTION

The present invention is directed to the prevention of disease transmission due to accidental sticks with contaminated medical needles and needle syringes. The apparatus of the present invention constitutes an improvement to standard medical injection devices, whether or not having injectable and/or retractable needles, which are possessed of a body member with a needle protruding from such body member.

In a first general embodiment, the present invention includes a raised bead, i.e. a protuberance, or member, or pellet, which is coaxially mounted upon the diameter of a needle at an axial position between the body member to which the needle is affixed and the tip of such needle. The raised bead is normally rigidly affixed by friction fit or adhesive directly to and upon the needle. The bead cooperates with a tubular sleeve which is coaxially positioned upon the needle. The tubular sleeve is adapted to slide along the length of the needle from a first position wherein the tip of the needle is exposed, thereby allowing normal patient injection, to a second position wherein the sleeve is engaged and retained by the bead in a position extending over the distal end of the needle, thereby sheathing the needle tip from accidental contact. The raised head thus serves as a locking member, or detent, to the slidable tubular sleeve.

In a further particular, preferred embodiment of the present invention, the raised bead is located at a region approximately midway along the length of the needle between the body member and the needle tip while the slidable tubular sleeve is sized to be approximately as long as one-half the length of the needle. It is further preferred that the raised bead should have external surface features which cooperatively engage complementary-shaped internal surface features formed within the slidable tubular sleeve in order to securely retain the sleeve in its second position (sheathing the tip of the needle) despite the application of forces tending to return the sleeve to its initial position (wherein the tip of the needle is exposed). The slidable tubular sleeve is preferably formed so as to be capable of being moved unidirectionally from a first detent at its first position proximate the body member, to a second detent at its second position sheathing the tip. Consequently, once the slidable tubular sleeve is slid into its sheathing position then the tip of the needle will not be advertently re-exposed.

Certain major variants of the embodiments of the present invention are possible. The basic embodiment of the invention includes only a raised bead serving as a locking member at a local position along a needle and a tubular sleeve sliding along such needle. The raised bead serves as a locking member, or detent, to the slidable tubular sleeve at its second position. However, the tubular sleeve may be held in its first position proximate the body member wherein the tip of the needle is exposed by detents. It may be held by several alternatives, either by (i) cooperative engagement with the raised bead (at that end of the slidable tubular sleeve which is distal, or toward the tip of the needle), or by (ii) cooperative engagement with the body member (which body member is at the proximal end of the tubular sleeve), or (iii) cooperative engagement at both ends. Further, regardless of the particular detent by which the slidable tubular sleeve is held in its first position, an end cap which sheaths the tip of the needle and which is removed prior to use of the needle may be maintained upon the (unused) needle. The end cap is so maintained by a detent resultant from (i) cooperative engagement with the locking bead by (ii) cooperative engagement with the slidable tubular sleeve, or by (iii) cooperative engagement with the body member.

The present invention is further embodied in particular methods for use of the several preferred apparatus embodiments of the invention. One method essentially includes (i) first performing an injection by holding the injection device body member with one hand and then (ii) sliding the tubular sleeve with the other hand along the needle to the second position engaging a detent wherein it protects the needle tip. By such a method a high degree of positive control is maintained over the position of the needle tip and there is improved avoidance that the injector should accidentally stick himself-/herself or other persons.

Finally, the present invention is further embodied in alternative methods of assembling the essential elements of a slidable tubular sleeve and a raised bead, or locking member, cooperatively interoperative with such sleeve onto a pre-existing needle, or syringe. Certain major variant methods proceed by steps conducted entirely from the distal end of such needle or syringe. By such assembly methods the benefits of the present invention in preventing accidental disease transmission from sticks with contaminated needles may be obtained while still employing standard, commercially available needles and syringes.

BRIEF DESCRIPTION OF THE DRAWINGS

These as well as other features of the present invention will become more apparent upon references to the drawings wherein:

FIG. 1 is a perspective view depicting in diagramatic form a first embodiment of the present invention.

FIG. 2 is an enlarged perspective view depicting the first embodiment of the present invention wherein a raised bead component or locking member is positioned along the length of a medical needle.

FIG. 3 is a cross-sectional view of the first embodiment of the present invention depicting the manner in which the slidable tubular sleeve is held at its first position proximate the body member of the injection device by a detent resultant from engagement with the body member.

FIG. 4 is an enlarged cross-sectional view depicting the proximal end region of an end cap of FIG. 3, which proximal end region presents an interior surface which mates with a complementary exterior surface formed on the raised bead in order to hold the end cap in a desired position.

FIG. 5 is an enlarged cross-sectional view depicting the proximal end region of the tubular sleeve, which proximal end region presents an interior surface which engages a complementary exterior surface of the raised bead in order to form a detent which holds the tubular sleeve in the second position sheathing the needle tip.

FIG. 6 is a partial cross-sectional view of the first embodiment of the invention depicting the slidable tubular sleeve in its second position wherein it sheathes the tip of the needle.

FIG. 7 is a perspective view depicting a second embodiment of the present invention wherein the raised locking bead includes particular cam and engagement surfaces which are positioned in alignment for cooperative engagement with complementary surfaces upon the interior of the slidable tubular sleeve.

FIG. 8 is a cross-sectional view of the second embodiment of the invention depicting the slidable tubular sleeve being held at its first position proximate the body member by a detent resultant from its engagement with the raised locking bead.

FIG. 9 is an enlarged partial cross-sectional view of the second embodiment of the present invention depicting the engagement of the slidable tubular sleeve and the locking bead when such tubular sleeve is disposed in its second detent position sheathing the tip of the needle.

DESCRIPTION OF THE PREFERRED EMBODIMENT

Figure 10:
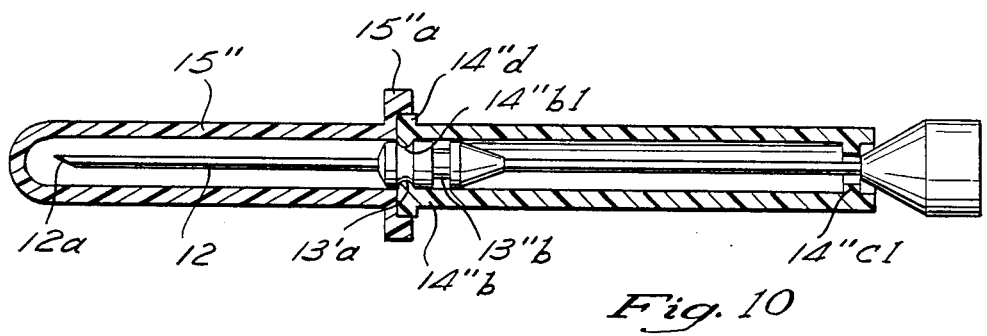
FIG. 10 depicts a third embodiment of the invention wherein the needle end cap is held in an initial position sheathing the needle tip by engagement with the slidable tubular sleeve.

As an overview, the present invention comprises a safety system for sheathing the contaminated tips of spent, i.e. used, medical needles in order to prevent transmission of disease resulting from accidental sticks. The invention is generally applicable to medical devices incorporating either solid or tubular needles. It is particularly applicable to hypodermic needles and syringes, vacuum tube phlebotomy systems having retractable needles, and intravenous devices having retractable needles.

Essential elements of an apparatus in accordance with the present invention are located relative to the needle and to the body member which mounts such needle to a syringe or the like. These elements are: (i) a raised bead or locking member which locally distends the diameter of the needle at a region between the body member supporting such needle and the needle tip, and (ii) a tubular sleeve positioned about the needle which slides along the needle from a first position proximate the body member wherein a tip of the needle is exposed for use to a second position wherein the tubular sleeve is retained by the raised bead, or locking member, to sheath the tip of the needle. The slidable tubular sleeve which is retained in the second, sheathing position by the raised bead or locking member solves the problem of recapping and/or separately disposing of a contaminated needle portion of a medical injection apparatus.

This is because the slidable tubular sleeve is rigidly positioned over the contaminated needle tip immediately after the use of the injection apparatus. After sheathing the needle the entire injection apparatus, and/or only the now-sheathed needle portion thereof, may be readily and safely disposed of (including by breaking the needle into a disposal container even while it is sheathed within the tubular sleeve).

With this overview in mind, a first embodiment of the present invention is illustrated in FIGS. 1 through 6. As depicted in FIG. 1, a medical injection apparatus is therein illustrated to be, for example, a hypodermic syringe basically consisting of a piston plunger 10 mounted into a body member 11 which mounts a hypodermic needle 12. The syringe and other medical injection devices mounting needles are readily available from suppliers Becton Dickinson and/or Sherwood, amongst other suppliers. In this first embodiment the present invention comprises the use of a spherically-shaped locking member or raised bead 13, which is rigidly affixed as by way of a press fit or adhesive at a position along the length of the needle 12 in order to locally increase the diameter or circumference of the needle. The raised bead 13 is normally located at the central region of the needle 12. This first embodiment of the present invention also comprises a tubular sleeve 14 which is coaxially mounted upon the needle 12 and adapted for selective reciprocal movement along the length of the needle 12. Preferably, although not required, the present invention further comprises an end cap 15 which covers the tip of the needle 12 at a time prior to use. In order to use the needle 12 the end cap 15 is summarily removed and discarded.

The detailed construction of the needle 12 and raised bead 13 may be observed in FIG. 2. The needle 12 is normally fabricated of surgical steel or like material. The raised bead 13, also referred to as a protuberance or locking member, is permanently affixed to and about the needle 12 at a fixed location. This location is normally approximately half-way along the length of such needle 12 between body member 11 and the needle tip 12a. The raised bead 13 may be formed integrally with the needle 12, and out of the same metal material, but this is difficult and not preferred. The raised bead 13 is normally formed from either ceramic or plastic material. It is either molded in situ around the body of needle 12, or slid upon the needle 12 from the distal end of such needle. In order that the very sharp tip 12a of the needle 12 should not be damaged during affixation of the bead 13 to the needle 12 by sliding over the tip, the internal diameter of the channel within the raised bead 13 is normally somewhat larger than the diameter of needle 12. Consequently, the raised bead 13 may ultimately have to be held in a desired position by the use of a modest amount of adhesive glue. All plastic, ceramic, and/or glue materials used to make and to attach the raised bead 13 and all other components of the apparatus of the present invention are inert to reaction with tissues and/or medicines in accordance with standards for materials used in medical injection devices. The entire injection apparatus including the needle 12 may normally be sterilized, or resterilized, with the raised bead 13 and slidable tubular sleeve 14 affixed thereto.

As depicted in FIG. 3, the tubular sleeve 14 is initially disposed in a first position upon the needle 12 wherein it is proximate to body member 11 and the tip 12a of needle 12 is exposed. The tubular sleeve 14 so disposed is initially held by engagement of its proximal end 14c (opposite the needle tip) with the body member 11. As shown in FIGS. 2 and 3, the end of the body member 11 reduces in diameter along a frustoconical surface 11a terminating in a small-diameter cylindrical end portion 11b having a circumferential groove or channel 11c formed therein. The groove 11c engages a complementary shaped flange 14c' upon the interior surface of proximal end 14c of the sliding tubular sleeve 14 (which feature is best shown in FIGS. 3 and 5). This engagement forms a first detent selectively maintaining the sleeve 14 upon the body member 11.

The tubular sleeve 14 observable in FIG. 3 is additionally preferably made of plastic and has an exterior end flange 14d adapted to be manipulated by the hand of a user. The external surface of the sleeve 14 is preferably formed in a smooth cylindrical surface, although grooves or other surface discontinuities may be provided to facilitate ready grasping by a hand of a user. The sleeve 14 includes an axially extending internal aperture 14a having a diameter slightly greater than the external diameter of the bead 13. The proximal end 14c of the tubular sleeve includes a reduced diameter aperture having a spherically-shaped recess 14c''' formed therein. The recess 14c''' is preferably sized to have a diameter equal to or slightly less than that of the bead 13 such that the bead 13 may be selectively received and retained therein when the sleeve 14 is selectively reciprocated from its first position to its second position as will be described infra.

The end cap 15 shown in FIG. 3 is preferably formed as a tubular plastic member having a closed distal end an open proximal end. The end cap is sized to possess an axial length sufficient to extend over from the bead 13 to beyond the tip 12a of the needle 12. The end cap 15 includes an interior ridge 15a defining an internal diameter sized slightly less than the maximum diameter of the bead 13. The engagement of interior ridge 15a and raised bead 13 forms a second detent which selectively maintains the end cap 15 upon the needle 12. As will be recognized by those having skill in the art, the end cap 15 may alternatively be mounted upon the bead 13 by way of frictional engagement with the outside diameter of the bead.

In further details of construction, the preferred configuration of the proximal end region internal surfaces of sliding tubular sleeve 14 may be observed in expanded detail in the cross-sectional view of FIG. 5. Closest to proximal end of the tubular sleeve 14, a ridge 14c' constricts the internal diameter of sliding tubular sleeve 14. Internal surfaces 14c4 and 14c5 present annular rings which are also of constricted diameter relative to the remaining portion of the aperture 14a of slidable tubular sleeve 14. Internal holding/retaining surface 14c3 presents an annular spherical surface which is complementary to the spherical surface of raised bead 13. Frustoconical surface 14c2 presents a ramp, or cam, from the larger diameter channel region 14a of tubular sleeve 14 to the distal end annular ring surface 14c5.

With the structure defined, the operation of the first embodiment of the present invention may be described. Initially when it is desired to use the syringe, a user grasps the body member 11 and/or the tubular sleeve 14 with one hand and grasps the end cap 15 with the other hand. By manually exerting a minor axial force upon the end cap 15 the flange 15a upon contact with the locking bead 13, flexes or deforms radially outward whereby the end cap 15 is axially slid over the bead 13 and off of the distal end of the needle 12.

No attempt is later made to replace cap 15 in order to shield a used and contaminated needle 12, this function is rather performed by the sliding of tubular sleeve 14 toward the distal end of needle 12 as described infra. It is additionally possible to remove cap 15 from needle 12 by a momentary, reciprocating movement of tubular sleeve 14. This movement is first in an axial direction to a position sufficiently over the raised bead 13 and toward the distal end of the needle 12 so that cap 15 is forced from the needle 12, but insufficiently far advanced toward the distal end of the need 12 so that the proximal end internal surfaces of the tubular sleeve 14 become engaged over the raised bead 13. The movement is then oppositely in the proximal direction to return the sleeve 14 to the position illustrated in FIG. 1.

At its initial first position shown in FIG. 3, the ridge 14c1 of the slidable tubular sleeve 14 compressively engages the complementary surface of the groove 11c upon body member 11. This engagement serves to retain the slidable tubular sleeve 14 in a mechanical detent at a position proximate to the body member 11, with the tip 12a of the needle 12 fully exposed.

Once the needle 12 has been used upon a patient in a conventional manner and is therefore contaminated, the slidable tubular sleeve 14 is merely slid to its permanent forward position sheathing the needle 12. It is so manipulated by being grasped between the fingers and pushed with a continuous motion axially along the length of the needle 12 toward the distal end thereof. In movement towrd the forward distal position, the surface of raised bead 13 cams upon the interior surface 14c2 of the slidable tubular sleeve 14, causing the diameter of the proximal end porton 14c to enlarge due to the moderate internal resiliency of the sleeve 14. This momentary enlargement thereby allows the bead 13 to become lodged in the spherical cavity defined by surface 14c3. To aid in this momentary diameter increase, one or more axial slits (not shown) may be formed in the proximal end portion 14c. Thus, the slidable tubular sleeve 14 is securely prevented from being slid entirely off the distal end of the needle 12 by the annular ring internal surface 14c4. Additionally, annular ring internal surface 14c5, just traversed by raised bead 13, is not easily traversed in the reverse direction due to the lack of any camming surface. Consequently the slidable tubular sleeve 14 will be securely held by a mechanical detent resultant from the frictional engagement of raised bead 13 and the complementary surface 14c3. The sleeve 14 will be retained at the distal end of the needle 12 sheathing tip 12a as illustrated in FIG. 6, despite any further application of axial forces.

A second variant embodiment apparatus of the present invention is shown in FIGS. 7-9. This embodiment apparatus is characterized, amongst other differences to the first embodiment, in that the slidable tubular sleeve 14' is maintained in its initial first position proximate the body member 11' by engagement with the raised bead 13' as opposed to engagement with the body member 11'. This is most clearly visible in FIG. 8, and should be contrasted to the alternative initial engagement of slidable tubular sleeve 14 with body member 11 which is shown in FIG. 3.

Additionally in the second variant embodiment, the raised bead 13' is possessed of a more complex shape than the spherical shape off raised bead 13 in the first embodiment shown in FIGS. 1-3 and comprises a small cylinder portion and an elongated spheroid portion, each of which includes a radially extending channel which engages a complementary contour within the interior channels of the slidable tubular sleeve 14' and/or end cap 15'.

In construction, the raised bead 13', best observable in FIGS. 7-9, presents at its distal end a circumferential radial groove 13'a which is of complementary configuration to the raised ridge 15'a formed within the internal aperture 15'b of end cap 15' near its proximal end. The raised bead 13' further presents a frustoconically-shaped surface portion 13'c at its proximal end, which surface 13'b increases in diameter in the distal direction terminating in a "U"-shaped circumferential channel 13'b positioned near the middle of the bead 13'. The square-shouldered circumferential channel 13'b of bead 13' at separate times serves to engage surfaces 14'b' and 14'c' which respectively serve to constrict the diameter of the internal aperture of slidable tubular sleeve 14' at its distal end region 14'b and proximal end region 14'c. More particularly, surface features 14'b1 as illustrated in FIG. 7 do not comprise an internal ridge similar to ridges 15a and 15'a, but rather comprise a plurality of small protrusions or tabs, preferably symetrically spaced, which constrict the internal diameter of slidable tubular sleeve 14' near the distal end thereof. These small tabs 14'b1 serve to engage circumferential channel 13'b formed on the bead 13' in order to form a detent mechanism holding the slidable tubular sleeve 14' in its initial, first position proximate the body member 11'. (as illustrated in FIG. 8).

In use, the end cap 15' is initially removed in an analogous manner to that described in relation to the first embodiment and after patient use of the needle 12 for medical injection purposes, the slidable tubular sleeve 14' is manually grasped at the proximal side of the flange 14'd. The sleeve 14' is then forced over the bead 13' toward the distal end of needle 12. The slidable tubular sleeve 14', which is normally plastic, is moderately resilient and expandable. Consequently, the tabs 14'b1 at the distal end region 14'c of tubular sleeve 14' during this sliding motion will be moderately deformed in an amount sufficient to exit channel 13'b, and will pass over the channel 13'a, of the bead 13' thereby allowing the sleeve 14' to slide fully toward the distal end of needle 12 in order to assume a position sheathing such needle.

Conversely to the tabs 14'b', the circumferential internal surface feature 14'c1 at the proximal end region 14'c of the tubular sleeve 14 comprise an annular flange or ridge having square shoulders as illustrated in FIG. 9. This ridge 14'c1 presents a strong retention force to complementary features which it engages. Thus, during the forward sliding of tubular sleeve 14', this internal annular ridge 14'c1 ramps against the cam presented by surface 14'c until it enters within circumferential channel 13'b of bead 13' wherein due to the resiliency of the ridge 14'c1, the ridge is captured within channel 13'b (as depicted in FIG. 9). In this position, any further sliding movement in either the distal or proximal axial direction is strongly resisted and thereby precluded by the mating engagement of such features. Consequently the needle 12 is permanently sheathed by the tubular sleeve 14' when the sleeve has been moved in the distal direction to assume its final, second position. At this time the sheathed needle 12 and/or the entire medical injection apparatus may be disposed. If it is desired that the sheathed needle 12 should be fractured from the body member 11' by breaking such needle off in an approved receptacle, then this operation may still be accomplished (by use of a properly sized receptacle orifice) while the slidable tubular sleeve 14' is maintained in position sheathing needle 12.

Figure 11:
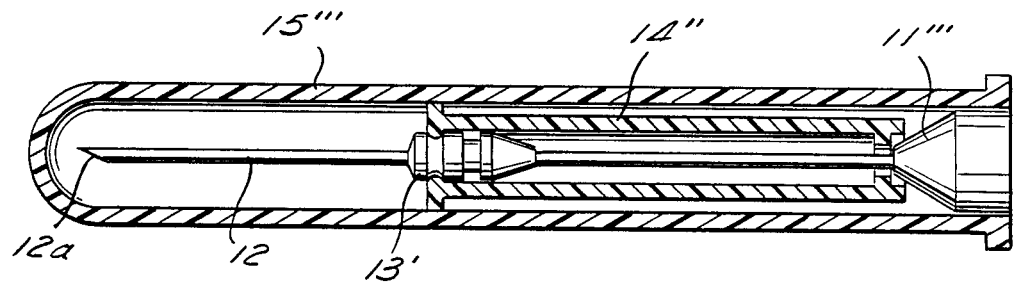
FIG. 11 depicts a fourth embodiment of the invention wherein a full-length needle cap is held in an initial position sheathing the entire needle by engagement with the body member of the injection device.

Third and fourth variant embodiments of the present invention particularly dealing with the size and manner of retention of the end cap are respectively shown in FIG. 10 and FIG. 11. It will be recognized that the end cap 15 illustrated in FIG. 3 and the end cap 15' illustrated FIG. 8 may readily be removed by either (i) grasping with the fingers and pulling the end cap from about the distal end of the needle 12, and/or (ii) forcing the end cap from its initial position retained upon needle 12 by a short reciprocating movement of slidable tubular sleeve 14 (14'). However, it is possible during an inadvertent careless removal of end cap 15 (15') to accidentally contact the exposed tip 12a of needle 12 during such removal of the cap. Consequently, it is desired insofar as is possible, that the end cap should be unseated from its original, protective position by a human motion which transpires as distantly as is possible from the tip 12a to needle 12. Even though the needle 12 is presumably unused and sterile at this time of removal of the end cap, it is of course desirable to avoid all needle sticks.

In accordance with these objectives, the third embodiment of the invention shown in FIG. 10 is similar in construction to the second embodiment except that the end cap 15" is held in its initial position sheathing the needle by engagement with a flange 14"d, which flange is somewhat reduced in size relative to flanges 14d and 14'd on slidable tubular sleeve 14", instead of by engagement with bead 13 or 13', respectively shown in FIG. 3 or 8. Additionally, it will be noted that the tabs 14"b1 constricting the internal diameter of slidable tubular sleeve 14" at the distal end region 14"b thereof are positioned to directly engage the distal-end circumferential groove 13'a of raised bead 13'. This should be contrasted to the previous position illustrated in FIG. 8 wherein tabs 14"b' engaged the circumferential channel 13'b of the bead 13'.

In operation, the proximal end flange 15"a of end cap 15" frictionally engages a complementary distal-end flange 14"d of the slidable tubular sleeve 14". The mating contact of these two flanges may be manually overcome by exerting moderate axial pressure against the proximal side of flange 15"a thereby unseating the same from its position sheathing needle 12". After use of the needle 12 the slidable tubular sleeve 14" is free (i.e. unrestricted) to be slid in the distal direction along the length of the needle 12 by manual pressure on the proximal side of the flange 14"d. This movement is continuous until such time as the flange 14"c1 enters into the complementary shaped channel 13"b from the locking bead or member 13" wherein further movement of the tubular sleeve is prevented and the tip of the needle is sheathed from contact.

A fourth variant embodiment of the present invention is illustrated in FIG. 11 and employs an end cap 15''' which is modified to completely encase the entire length of the needle 12, the raised bead 13', and the slidable tubular sleeve 14'. This end cap 15''' is retained in its initial position sheathing the needle 12 by a frictional engagement, which may optionally include the provision of complementary mating surfaces, with the external circumference of body member 11''' near the distal end thereof. This complete cap 15''' is readily and safely removed by finger contact occurring at or near the location of its temporary affixment to body member 11'''. Thereafter both the use of the needle 12 and the subsequent sheathing of the needle 12 with slidable tubular sleeve 14'' transpires in analogous manner to that previously described. The full needle sheath 15''' shown in FIG. 11 presents an improved potential to maintain the needle 12, the raised bead 13', and the slidable tubular sleeve 14' in a sterile condition prior to use. The temporary affixment of cover 15''' to body member 11''' may be made air tight and frangible so as to permit removal of the cover 15''' at such time as the injection apparatus is to be placed in use.

Figure 12:
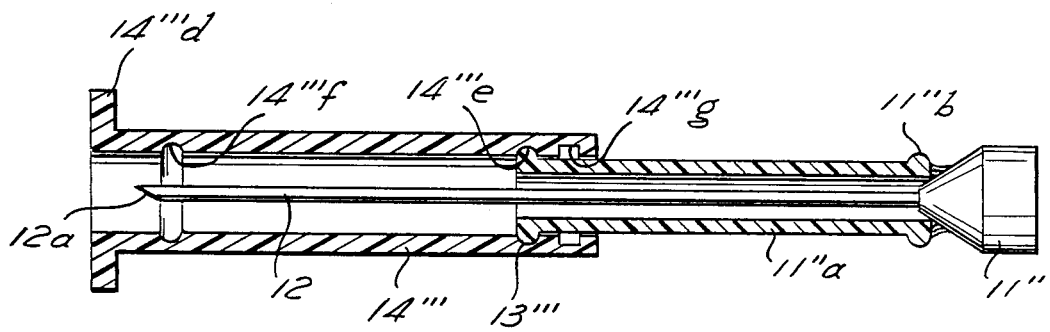
FIG. 12 is a cross-sectional view depicting a fifth embodiment of the present invention wherein the locking component comprises a tubular appendage affixed to the body member and extending along length of the needle, and wherein the slidable tubular sleeve is axially reciprocated relative to the appendage to sheath the needle.

A still further, fifth variant embodiment of the present invention is shown in FIG. 12 which comprises a pair of telescoping sleeves mounted to the body member, which are adapted to sheath the entire length of the needle. In this fifth embodiment, the raised bead which is located along the length of needle between the body member mounting such needle and the needle tip, and wich locally distends the diameter of the needle, is not directly affixed to the needle but is instead mounted upon a tubular appendage which extends along the needle and is affixed to the same body member to which the needle affixes. In particular, in this embodiment, the raised bead 13'' comprises a raised flange positioned at the distal end of the tubular appendage or sleeve 11''a attached to body member 11''. This sleeve includes an axial aperture having an internal diameter greater than the external diameter of needle 12 and an external diameter which is (except in the region of raised bead 13'') slightly greater than the inside diameter of the sliding tubular sleeve 14'''. The sleeve or tubular appendage 11a'' is assembled in a telescoping relationship with the tubular sleeve 14''' as depicted in FIG. 12.

The sliding tubular sleeve 14''' is shown in FIG. 12 at its initial detent position. More particularly, the sliding tubular sleeve 14''' is held in this initial, first position sheathing the tip 12a of needle 12 by a mechanical detent resultant from engagement of raised head 13''' with an internal circumferential groove 14'''e formed on the internal diameter of slidable tubular sleeve 14''' at its proximal end region.

When it is desired to use the needle, the sliding tubular sleeve 14''' is telescoped or slid relative to the tubular appendage to assume a second position wherein it is momentarily retained by a mechanical detent resultant from either (i) an engagement of optional internal circumferential groove 14'''f with raised bead 13''', or (ii) engagement of internal circumferential channel 14'''g with an optional external circumferential ridge 11''b, or (iii) an engagement of groove 14'''f with raised bead 13''' simultaneously with an engagement of grooved channel 14'''g to ridge 11''b such that the needle tip is exposed for injection into a patient. In simplest terms, the sliding tubular sleeve 14''' may engage a mechanical detent at (i) its distal end region, or (ii) its proximal end region, or (iii) both its distal and proximal end regions. If a proximal end region detent is used by causing an external circumferential ridge 11''b to engage with internal circumferential channel 14'''g, then care must be used to make sure that this detent is not so strong as to prevent subsequent intended reciprocal movement of slidable tubular sleeve 14''' in the distal direction. Particularly, external circumferential ridge 11''b will not normally be of equally large diameter as raised bead 13''' nor will it engage circumferential channel 14'''g so tightly as will raised bead 13''' in the manner next explained.

After conventional injection use of the needle 12, the sliding tubular sleeve 14''' is held with the fingers on the proximal side of flange 14'''d and is axially pushed or telescoped in the distal direction until internal circumferential channel 14'''g engages the raised flange 13'''. The sliding tubular sleeve 14''' is again retained or captured, now very securely, by a mechanical detent resultant from this engagement. It is thereby permanently held in a third position again sheathing the tip 12a of needle 12.

Obviously this fifth embodiment of the present invention shown in FIG. 12 presents interesting variations involving (i) the detail nature of locking member 13''' connected to and part of appendage 11''a, (ii) the engagement of sliding tubular sleeve 14''' (which is equally susceptible to engage fillet types 13 and 13'), and (iii) the mode and manner of operating the apparatus of the invention. Less obviously, it must be recognized that feature 13'' need not exclusively be a raised bead which engages internal circumferential grooves and channels 14'''e, 14'''f, and 14'''g to slidable tubular sleeve 14'''. Rather, the feature 13'' could itself be, instead of a raised bead, an indented groove or channel on the distal end of appendage 11''a. This groove/channel forming an indented feature 13'' would engage complementary surfaces in the form of ridges on the interior of slidable tubular sleeve 14'''. In a like manner many of the engagement geometrics within the apparatus embodiments of the present invention will be understood to be capable of being reversed.

The present invention is further embodied in methods for fabricating the preferred embodiments defined above. Major variants for fabrication of the apparatus of the present invention which proceed exclusively from the distal end of the needle are readily and efficiently accomplished. In a first distal end assembly method, the locking bead, or member 13 may be either (i) slid onto needle 12 with the needle entering a pre-existing axial channel within the bead or (ii) molded in situ about and upon needle 12. Then the tubular sleeve 14 may be slipped over the needle 12, and forced over the raised bead 13 which is now affixed to such needle 12, until it assumes the first detent position illustrated in FIG. 3. This forced assembly may be accomplished with the use of precision jigs, if desired or required. It is accomplished without damage to the function of the apparatus of the present invention for sheathing the tip 12a of needle by sliding the tubular sleeve 14.

Alternatively, as a second distal end assembly method, the tubular sleeve 14 is first slid the length of needle 12, and secured at its first detent position approximate to body member 11. Then the raised bead 13 is affixed by sliding or molding onto needle 12 at a position immediately toward the distal end of such needle 12 from the end of tubular sleeve 14.

Alternatively, as a third distal end assembly method, the bead 13 which possesses an axial central channel is placed within a constricted region of the internal channel of a tubular sleeve member 14 so that the internal axial channels of both the tubular sleeve and the bead are coaxial. The bead 13 is internally retained thereby within internal channel of the tubular sleeve 14 at a region along such sleeve which is either near its distal or proximal end. However, if the bead 13 is initially retained in the proximal end region constricted internal channel of the tubular sleeve (as the tubular sleeve 14 and bead 13 are illustrated to be aligned in FIG. 6) then the tubular sleeve 14 must still be slid to its first detent position proximate to body member 11 after further assembly. Such further assembly transpires as the sliding insertion of the needle 12 along the coaxial channels of the tubular sleeve 14 and at the bead 13 held within the sleeve. The needle 12 is inserted within the channels until the bead 13 assumes the appropriate position along the needle, and becomes the raised bead 13 thereafter permanently affixed to the needle 12.

Finally, as a fourth distal end assembly method, a first, thin-walled, tubular sleeve 11a which is both shorter than the needle 12 and of greater internal diameter than the external diameter of the needle 12 may be slid over and upon the needle until it abuts against body member 11. It may then be permanently affixed to the body member 11 such as by sonic welding or gluing. Such an attached first sleeve 11a is illustrated in FIG. 12 as raised bead 13". Then in the assembly method, a second sleeve 14", also shorter than the needle and with an internal diameter which is slightly smaller (greater) than the external diameter of the first sleeve save for a distal end region, a proximal end region, or both a distal end proximal end region whereat the internal diameter is slightly greater (smaller) then the external diameter of the first sleeve, is slid over the needle 12 and the raised bead 13" (shown in FIG. 12) until the raised bead 13" engages complementary features upon this second sleeve and retains it in position as the slidable sleeve 14" (shown in FIG. 12). As will be recognized, this assembly methodology is especially beneficial for retrofitting existing needle constructions since assembly may be accomplished wholly without touching the needle 12 and particularly without touching the needle tip 12a as well as not requiring a specially formed body member 11.

Other variants of assembly methods for realizing the apparatus of the present invention, especially diverse assembly method proceeding from the proximal end of the needle 12 prior to the affixation of body member 11, will suggest themselves to practitioners in the mechanical arts. A principal feature of the four different methods for assembling the apparatus of the present invention exclusively from the distal end of the needle is that such assembly may transpire upon pre-existing conventional syringe or medical injection devices. Consequently, the manufacture and assembly of the present invention should be perceived to be pertinent to retrofit of pre-existing injection devices as well as to the fabrication of wholly new injection devices incorporating the principles of the present invention.

In accordance with the preceding discussion, the present invention should be perceived to broadly encompass the provision of a slidable tubular sleeve to and upon a needle of a medical injection apparatus. It has been taught how to retain this slidable tubular sleeve in an initial position wherein the injection device needle may be operatively used, and in a final position wherein the injection device needle is sheathed after use in order to protect against disease transmission due to accidental needle pricks. Several variants in the detailed manner of the retention of the sliding tubular sleeve, the manufacture of the apparatus of the invention, and the cooperative interaction of the features of the invention have each been shown.

Further variants in the detailed implementation, manner of construction, and cooperative interrelationship of the present invention with diverse medical injection apparatus will suggest themselves to a practitioner in the arts of medical injection device design in accordance with the principles of the present invention. For example, the raised beam might not be "raised", but rather comprise an indented feature within a particularly thick needle. Such an indented feature would cooperatively engage a complementary surface within the internal channel of a sliding sleeve in an equivalent manner to the engagement performed by the preferred embodiment apparatuses of the present invention.

For example, the raised bead might be somewhat obscured through being, instead of an exclusively local protruberance upon the shaft of the needle, an extended and enlarged region. These and other such additional variants as may be readily imagined do not obscure the basic principles of the present invention for sliding and retaining a sliding sheath along and upon a needle of a medical injection apparatus.

Therefore, the present invention should be interpreted in accordance with the scope of the following claims, only, and not merely in accordance with the particular preferred embodiments—numerous as such embodiments may be—within which the invention has been taught.

What is claimed is:

1. In an injection apparatus having a body member and needle protruding from the body member, an improvement comprising:
   a locking member affixed to the length of the needle sized to locally increase the diameter of the needle at a location interposed between the body member and the tip of the needle; and
   a tubular sleeve disposed along the length of the needle which slides along the length of the needle from a first position whereat the tip of the needle is exposed to a second position whereat the sleeve is securely retained by the locking member to sheath the tip of the needle.

2. The injection apparatus improvement according to claim 1 wherein the locking member is located at a region approximately midway along the needle between the body member and the tip.

3. The injection apparatus improvement according to claim 1 wherein the locking member has an external surface cooperatively interoperative with a complementary internal surface within the tubular sleeve to securely retain the sleeve in the second position.

4. The injection apparatus improvement according to claim 1 wherein the locking member is formed upon an appendage affixed to the body member and the tubular sleeve is telescopingly mounted upon said appendage.

5. The injection apparatus improvement according to claim 1 wherein the sleeve in its region proximal the tip of the needle is of a first internal diameter greater than the external diameter of the locking member, and is in a region of the sleeve proximal the body member of a second, internal diameter smaller than said first diameter which when positioned about the locking member, serves to tightly engage the locking member.

6. The injection apparatus improvement according to claim 5 wherein that second internal diameter is formed to tightly engage a region of the body member.

7. The injection apparatus improvement according to claim 5 wherein the exterior surface of the locking member and the interior surface at the sleeve present complementary features to capture said sleeve about said locking member.

8. The injection apparatus improvement according to claim 1 wherein the sleeve in its central region is of a first internal diameter greater than the external diameter of the locking member, and in separate regions of the sleeve adjacent the tip of the needle and the body member are of second, smaller internal diameters which second diameters each serve to tightly engage the locking member when positioned thereabout.

9. The injection apparatus improvement according to claim 8 wherein the exterior surface of the locking member, and each of the interior surfaces of the sleeve at each of the separate regions, present complementary features sized to tightly engage the locking member.

10. The injection apparatus improvement according to claim 1 wherein the external surface of the sleeve presents a surface for movement from the first to the second position.

11. The injection apparatus improvement according to claim 10 wherein the external surface of the sleeve includes a flanged formed to facilitate manipulation by a user.

12. The injection apparatus improvement according to claim 11 wherein the external surface of the sleeve is formed to include irregularities adapted to be grasped by a user.

13. The injection apparatus improvement according to claim 1 further comprising:
a cap positioned about the tip of the needle when the tubular sleeve is at the first position and retained in this position about the tip of the needle by the locking member.

14. The injection apparatus improvement according to claim 1 further comprising:
a cap positioned about the tip of the needle when the tubular sleeve is at the first position and retained in this position about the tip of the needle by the tubular sleeve.

15. The injection apparatus improvement according to claim 1 further comprising:
a cap positioned about the tip of the needle when the tubular sleeve is of the first position and retained in this position about the tip of the needle by the body member.

16. An injection apparatus comprising:
a body member;
a needle having a proximal and distal end, said needle affixed to the body member adjacent its proximal end and extending outwardly therefrom;
protuberance means mounted in a fixed position along the length of the needle between said body member and the distal end of said needle; and
a cylindrical sleeve,
which is shorter than the needle and substantially coaxial with the needle slidable along the length of the needle,
which is moved from a first detent position along the length of the needle, in which position the distal end of the needle is exposed to a second detent position along the length of the needle, in which position the distal end of the needle is sheathed, by the sleeve.

17. The injection apparatus according to claim 16 wherein the protuberance means is coaxially positioned about the needle.

18. The injection apparatus according to claim 16 wherein the tubular sleeve is also held in the first position by the protuberance means.

19. The injection apparatus according to claim 16 further comprising:
an end cap sheathing the tip of the needle when the sleeve is at the first detent position and which is removed when the sleeve is at the second detent position.

20. The injection apparatus according to claim 19 wherein the end cap is held sheathing the tip of the needle by the protuberance means.

21. The injection apparatus according to claim 19 wherein the end cap is held sheathing the tip of the needle by the tubular sleeve.

22. The injection apparatus according to claim 19 wherein the end cap is held sheathing the tip of the needle by the body member.

23. An injection apparatus comprising:
a body member;
a needle which is affixed to the body member;
a protuberance interposed along the length of the needle; and
a tubular sleeve, which is shorter than the length of the needle and disposed substantially coaxial with the needle, said sleeve slidable along the length of the needle, which is at a first time held in a first detent position along the length of the needle, in which position the tip of the needle is exposed; and
which is at a second time locked in a second detent position along the length of the needle, in which the position the tip of the needle is sheathed.

24. The injection apparatus according to claim 23 wherein the protuberance comprises a radially extending locking member coaxially positioned upon the needle.

25. The injection apparatus according to claim 23 wherein the tubular sleeve is also held in the first position by the body member.

26. The injection apparatus according the claim 23 further comprising:
an end cap sheathing the tip of the needle when the sleeve is at the first detent position and which is removed when the sleeve is at the second detent position.

27. The injection apparatus according to claim 26 wherein the end cap is held sheathing the tip of the needle by the protruberance.

28. The injection apparatus according to claim 26 wherein the end cap is held sheathing the tip of the needle by the tubular sleeve.

29. The injection apparatus according to claim 26 wherein the end cap is held sheathing the tip of the needle by the body member.

30. A method of retrofitting a sliding guard onto an injection needle comprising:
sliding in a first direction a small pellet of an annular ring cross-section, which pellet has a pre-existing internal axial channel of sufficient diameter to accommodate an injection needle, onto and along the needle to a position between the needle tip and the body member;
affixing the pellet to the needle;
sliding in the first direction a tubular sleeve, which sleeve has a central region with an internal diameter which is greater than the external diameter of the pellet and which sleeve has regions proximate each end having internal diameters which are substantially equal to the external diameter of the pellet, onto and along the needle and across the pellet affixed thereto until one end region of the sleeve is proximate the body member while the other end region of the sleeve engages the pellet by relatively tightly contacting the external diameter of the pellet;

wherein the engaged sleeve is held in a first detent position along the needle proximate the body member and exposing the needle tip; and wherein the engaged sleeve may be forcibly slid in a second direction, opposite to the first direction, from the first detent position in a path along the needle and across the pellet affixed thereto until the one end of the sleeve engages the pellet, thereafter holding the sleeve in a second detent position whereat the needle tip is sheathed;

whereby the cylindrical sleeve sliding in a first direction to a first detent position exposing the needle tip, and in a second direction to a second detent position sheathing the needle tip, constitutes a sliding guard to the injection needle.

* * * * *